United States Patent
Klocke et al.

(10) Patent No.: US 8,623,073 B2
(45) Date of Patent: Jan. 7, 2014

(54) DEGRADABLE METAL STENT HAVING AGENT-CONTAINING COATING

(75) Inventors: Bjoern Klocke, Zurich (CH); Tobias Diener, Erlangen (DE); Matthias Fringes, Ansbach (DE); Claus Harder, Uttenreuth (DE)

(73) Assignee: BIOTRONIK VI Patent AG, Baar (CH)

( * ) Notice: Subject to any disclaimer, the term of this patent is extended or adjusted under 35 U.S.C. 154(b) by 498 days.

(21) Appl. No.: 12/179,183

(22) Filed: Jul. 24, 2008

(65) Prior Publication Data

US 2009/0030507 A1    Jan. 29, 2009

(30) Foreign Application Priority Data

Jul. 24, 2007    (DE) .................. 10 2007 034 364

(51) Int. Cl.
*A61F 2/06*    (2013.01)
(52) U.S. Cl.
USPC .................. 623/1.46; 623/1.42; 623/1.44
(58) Field of Classification Search
USPC .............. 623/1.15, 1.42, 1.44, 1.46
See application file for complete search history.

(56) References Cited

U.S. PATENT DOCUMENTS

| | | | | |
|---|---|---|---|---|
| 7,632,307 B2* | 12/2009 | Pacetti et al. | ........ | 623/1.44 |
| 7,828,840 B2* | 11/2010 | Biggs et al. | ........ | 623/1.44 |
| 7,951,194 B2* | 5/2011 | Gueriguian et al. | ........ | 623/1.44 |
| 7,955,383 B2* | 6/2011 | Krivoruchko et al. | ........ | 623/1.44 |
| 8,057,534 B2* | 11/2011 | Boismier et al. | ........ | 623/1.38 |
| 8,147,539 B2* | 4/2012 | McMorrow et al. | ........ | 623/1.46 |
| 8,252,046 B2* | 8/2012 | Shulze et al. | ........ | 623/1.42 |
| 8,518,100 B2* | 8/2013 | Consigny et al. | ........ | 623/1.15 |
| 8,523,938 B2* | 9/2013 | Takeuchi et al. | ........ | 623/1.46 |
| 2004/0024448 A1* | 2/2004 | Chang et al. | ........ | 623/1.42 |
| 2004/0062592 A1 | 4/2004 | Shekalim et al. | | |
| 2004/0215313 A1* | 10/2004 | Cheng | ........ | 623/1.11 |
| 2005/0038505 A1* | 2/2005 | Shulze et al. | ........ | 623/1.42 |
| 2006/0093643 A1 | 5/2006 | Stenzel | | |
| 2006/0095123 A1* | 5/2006 | Flanagan | ........ | 623/1.46 |
| 2006/0149365 A1* | 7/2006 | Fifer et al. | ........ | 623/1.46 |
| 2006/0198869 A1 | 9/2006 | Furst et al. | | |

(Continued)

FOREIGN PATENT DOCUMENTS

| | | |
|---|---|---|
| DE | 10235689 A1 | 2/2004 |
| DE | 29724864 U1 | 11/2004 |

(Continued)

OTHER PUBLICATIONS

Search Report for German Patent Application No. 10 2007 034 364.9; Apr. 1, 2008.

(Continued)

*Primary Examiner* — Thomas J Sweet
*Assistant Examiner* — Seema Mathew
(74) *Attorney, Agent, or Firm* — Biotech Beach Law Group, PC

(57) ABSTRACT

A stent comprising a degradable metal stent main body; a partition layer which is applied to the surface of the stent main body so that at least parts of the surface of the luminal side are not covered; and an agent-containing layer which is applied to the surface of the partition layer at least partially on the abluminal side of the stent main body and comprises one or more agents and possibly one or more polymers.

18 Claims, 6 Drawing Sheets

(56) References Cited

U.S. PATENT DOCUMENTS

| | | |
|---|---|---|
| 2006/0224237 A1 | 10/2006 | Furst et al. |
| 2006/0241742 A1* | 10/2006 | Harder et al. ............... 623/1.42 |
| 2007/0050009 A1 | 3/2007 | Flanagan |
| 2007/0129789 A1* | 6/2007 | Cottone et al. .............. 623/1.41 |
| 2008/0071355 A1* | 3/2008 | Weber et al. ................ 623/1.16 |
| 2008/0147165 A1* | 6/2008 | Hossainy et al. ............ 623/1.15 |
| 2008/0215139 A1* | 9/2008 | McMorrow et al. ......... 623/1.43 |
| 2008/0215141 A1* | 9/2008 | Hossainy .................... 623/1.46 |
| 2009/0005861 A1* | 1/2009 | Hossainy et al. ............ 623/1.46 |
| 2009/0148496 A1* | 6/2009 | Schmitz et al. .............. 424/426 |
| 2009/0264975 A1* | 10/2009 | Flanagan et al. ............. 623/1.2 |
| 2010/0137977 A1* | 6/2010 | Gregorich et al. ........... 623/1.42 |
| 2012/0010698 A1* | 1/2012 | Hwang et al. ............... 623/1.42 |
| 2012/0323308 A1* | 12/2012 | Zhou .......................... 623/1.16 |

FOREIGN PATENT DOCUMENTS

| | | |
|---|---|---|
| DE | 102005010998 A1 | 6/2006 |
| DE | 102005018356 A1 | 10/2006 |
| DE | 102005021622 A1 | 11/2006 |
| DE | 102006038235 A1 | 2/2008 |
| DE | 102006038239 A1 | 2/2008 |

OTHER PUBLICATIONS

Search Report for European Patent Application No. 08158778.4; Oct. 29, 2008.

\* cited by examiner

DEGRADABLE METAL STENT HAVING AGENT-CONTAINING COATING

PRIORITY CLAIM

This patent application claims priority to German Patent Application No. 10 2007 034 364.9, filed Jul. 24, 2007, the disclosure of which is incorporated herein by reference in its entirety.

FIELD

The present disclosure relates to a stent comprising a degradable metal stent main body and an agent-containing coating which is applied to the stent main body. The present disclosure further relates to a method for producing the stent, a method for the spatial separation of degradation products of a degradable metal stent main body, one or more agents which are applied to the stent, and the use of a stent according to the present disclosure.

BACKGROUND

Stents in general are endovascular prostheses and/or implants which are used for treating stenoses, for example. Stents are additionally known for the treatment of aneurysms. Stents fundamentally have a support structure which is capable of supporting the wall of a vessel to widen the vessel and/or bypass an aneurysm.

For this purpose, stents are inserted in a compressed state into the vessel and then expanded at the location to be treated and pressed against the vascular wall. This expansion may be performed with the aid of a balloon catheter, for example. Alternatively, self-expanding stents are also known in the art. These stents are constructed from a superelastic metal, such as Nitinol, for example.

Stents are currently classified in two main types, the non-degradable (permanent) stents and the (bio)degradable stents. Nondegradable stents are designed such that they remain in the vessel for an unspecified period of time. (Bio)degradable stents (hereinafter referred to as "degradable" stents), in contrast, are degraded over a predetermined period of time in a vessel. Degradable stents are preferably first degraded when the traumatized tissue of the vessel is healed, a support function is no longer necessary, and the stent no longer has to remain in the vascular lumen.

However, it has been shown that side effects, such as restenosis and thromboses, may occur due to the introduction of stents into vascular systems.

For this reason, stents have been developed which contain one or more agents which are discharged to the organism, as well as to the support structure, upon or after implantation in the vascular system.

Known stents coated with agent have a coating, the support structure of the stent typically being coated with an agent-containing polymer on both the luminal and also the abluminal (mural) surface.

The release of the agents from the polymer matrix typically results via diffusion processes and/or erosion processes of the polymer matrix.

In stents whose luminal and abluminal surfaces have been coated with growth-inhibiting antiproliferative agents, it has been established that the endothelialization of the stent (overgrowth of the stent with vascular cells) is slowed or prevented and the risk of a thrombosis is thus increased.

In a stent having magnesium alloy, the pH value of the magnesium stent implanted in a vessel rises in the immediate surroundings of the support structure because of the $Mg(OH)_2$ formation as a result of the degradation. Such a pH value shift into the basic range may be particularly harmful for pH-unstable agents, in particular, rapamycin and paclitaxel.

If polymer material (e.g., polyester) degradable by hydrolysis is used as the matrix for the agent coating, the pH value of a stent implanted in a vessel sinks as a result of the hydrolysis of the degradable polymer and formation of the corresponding acids (lactic acid, glycolic acid, and the like). In particular, the decomposition speed of a degradable metal stent main body may be negatively influenced by the pH value shift into the acid range.

SUMMARY

One feature of the present disclosure provides a degradable metal stent charged with at least one agent. One aspect of the present disclosure is to provide a stent with improved stability of the agent notwithstanding the presence of the degradation products of the stent materials, in particular, stent main body materials, and/or the endothelialization of the stent being improved.

The present disclosure describes several exemplary embodiments of the present invention. One aspect of the present disclosure provides a stent, comprising a) a degradable metal stent main body, b) a partition layer which is applied to the surface of the stent main body so that at least parts of the surface of the luminal side are not covered, and c) an agent-containing layer which is applied to the surface of the partition layer at least partially on the abluminal side of the stent main body, the stent containing a layer comprising one or more agents.

The coating of the stent according to the present disclosure is accordingly designed in such a way that the stent struts are only in contact with the partition layer b) and not with the agent layer c). Accordingly, the partition layer b) is situated precisely between the stent main body and the agent layer c) or, in a further design, may project beyond the partition area between stent main body and agent layer. In a stent according to the present disclosure, the partition layer b) is applied to the surface of the metal stent main body in such a manner that at least parts of the surface of the luminal side of the stent main body are not covered by the partition layer b), so that the degradation of the stent main body on the luminal side may begin upon or after implantation in a human or animal body.

For this purpose, the preferred designs of the stent according to the present disclosure may be provided all together, partially—in arbitrary combination, and individually.

Another aspect of the present disclosure provides a method for producing a stent, comprising a) providing a degradable metal stent main body and a first preparation which comprises one or more substances, b) coating the surface of the stent main body with the first preparation so that a partition layer is formed, at least a part of the surface of the luminal side not being covered, c) providing a second preparation which comprises one or more agents, and d) coating the surface or parts of the surface of the partition layer on the abluminal side of the stent main body with the second preparation so that an agent-containing layer is formed.

A further aspect of the present disclosure provides a method for the spatial separation of degradation products of a degradable metal stent main body and one or more agents and possibly one or more degradable polymer layers which are applied to a stent during or after implantation in a human or animal body, the method comprising a) providing a stent having (i) a degradable metal stent main body, (ii) a partition layer which is applied to the surface of the stent main body so that at least a part of the surface of the luminal side are not covered, and an agent-containing layer which is applied to the surface of the partition layer at least partially on the abluminal side of the stent main body, the agent containing layer comprising one or more agents; and b) implanting the stent in a human or animal body.

An additional aspect of the present disclosure provides a method of using a stent having a partition layer which is applied to the surface of the stent main body so that at least parts of the surface of the luminal side are not covered for the spatial separation of degradation products of the stent main body on one hand and the agents and possibly degradation products of the first polymer layer on the other hand during or after implantation of the stent in a human or animal body.

The present disclosure is based on the finding that a spatial separation of the agents and possibly the degradation products of an agent-polymer coating on one hand and the degradation products of the degradable metal stent main body on the other hand may be achieved upon implantation of the stent in a vessel by the coating of the stent with a partition layer between stent main body and agent layer, possibly having a polymer matrix.

An advantage of the invention of the present disclosure is that the degradation products of the stent may not exert an influence on pH-unstable agents because the partition layer spatially separates the degradation products of the stent from the agents. A further advantage of the invention of the present disclosure is that, if the agents are incorporated in a polymer matrix, the degradation products of the polymer matrix have no disadvantageous effect on the degradation speed of the degradable stent because the partition layer is also designed such that the degradation products of a polymer-containing agent layer are spatially separated from the stent main body.

Finally, a further advantage of the invention of the present disclosure is that the stent is endothelialized more rapidly, i.e., overgrown by endothelial cells (EC) more rapidly, because known (nondegradable and degradable, preferably magnesium-containing) metal surfaces, in contrast to surfaces coated to be antiproliferative using rapamycin or paclitaxel, are typically nearly completely populated by EC within a few days or weeks. In particular, it has been shown that magnesium surfaces even endothelialize significantly more rapidly than surfaces made of typical metallic main body materials, such as medical steel (316L) or cobalt-chromium alloys. The danger of late thromboses, as may be observed, in particular, in agent-releasing stents of the prior art, is reduced by more rapid and complete overgrowth with endothelium.

A further advantage of the more rapid endothelialization is that the agents intended for the vascular wall are not delivered or are only delivered in such a small amount to the vascular lumen so that the agent concentrations at the desired location are higher and more reproducible.

The exemplary embodiments of the stent according to the present disclosure described hereinafter can be applied to the particular features of the present application according to the present disclosure.

According to the present disclosure, the materials of the stent main body typically comprise degradable metal and/or degradable metal alloys.

For purposes of the present disclosure, "degradable metal stent" means that the metal stent is degraded in physiological surroundings, in particular, in the vascular system of the human or animal body, in such a way that the stent loses its integrity.

The degradable metallic material is preferably a biocorrodible alloy, the main components of the alloy being selected from the group consisting of magnesium, iron, zinc, and tungsten. In particular, a magnesium alloy is preferable as a degradable metallic material.

The alloy, in particular, comprising magnesium, iron, zinc, and/or tungsten, is to be selected in its composition so that the alloy is biocorrodible. For purposes of the present disclosure, "biocorrodible" alloys mean alloys in which degradation occurs in physiological surroundings, which finally results in the entire stent or the part of the stent formed from the material losing its mechanical integrity. For purposes of the present disclosure, an alloy means a metallic structure whose main component is magnesium, iron, zinc, or tungsten. The main component is the alloy component whose weight proportion in the alloy is highest. A proportion of the main component is preferably more than 50 wt.-%, more preferably more than 70 wt.-%. A magnesium alloy is preferred.

If the material is a magnesium alloy, the material preferably contains yttrium and further rare earth metals because an alloy of this type is distinguished due to its physiochemical properties and high biocompatibility, in particular, also its degradation products.

Magnesium alloys of the WE series, in particular, WE43, as well as magnesium alloys of the composition rare earth metals 5.2-9.9 wt.-%, thereof yttrium 3.7-5.5 wt.-%, and the remainder <1 wt.-% are especially preferable, magnesium making up the proportion of the alloy to 100 wt.-%. These magnesium alloys have already confirmed their special suitability experimentally and in initial clinical trials, i.e., they display a high biocompatibility, favorable processing properties, good mechanical characteristics, and corrosion behavior adequate for the intended uses. For purposes of the present disclosure, the collective term "rare earth metals" includes scandium (21), yttrium (39), lanthanum (57) and the 14 elements following lanthanum (57), namely cerium (58), praseodymium (59), neodymium (60), promethium (61), samarium (62), europium (63), gadolinium (64), terbium (65), dysprosium (66), holmium (67), erbium (68), thulium (69), ytterbium (70) und lutetium (71).

All possible and typical stent geometries are usable as the stent geometries. Preferably, the web or strut cross sections are to be identical at all points of the stent. The web or strut cross sections are preferably rectangular by which the coating with the partition layer, the agent-containing layer, and the third polymer layer, which may also be referred to as a topcoat, is simplified. Such cross sections are typical for stents which are, typically, cut into shape by laser from tubular starting material. The edges may be rounded and the surfaces smoothed by subsequent electropolishing. Alternatively, oval cross sections of the webs or struts of the metal stent main body may be used, as occur in welded stents which are sold, in particular, by Medtronic.

For purposes of the present disclosure, "luminal side of the surface of a stent main body" means the surface of a stent main body which is predominantly in contact with the vascular lumen and thus with the vascular fluid. In other words, in a typical cylindrical stent, this is the internal face in the direction of the central cylinder axis.

For purposes of the present disclosure, "abluminal side of the stent main body" means the surface of the stent main body which is in contact with the vascular tissue. In other words, in the typically cylindrical stent, this is the external cylindrical surface.

The various designs for the abluminal coating of the stent main body and/or for a coating of the surface of the stent main body, at least parts of the luminal surface not being coated by partition layer b) (2), agent-containing layer c) (3), and third polymer layer d) (4), are shown in the figures, in particular.

The agents are discharged from the stent main body to the vascular tissue so that the agents may act effectively against neointimal proliferation. For example, paclitaxel is to be discharged in a few seconds up to a few days to the vessel. For sirolimus and related limus compounds, such as zotarolimus, tacrolimus, everolimus, biolimus, in particular biolimus A9, the agent is to be discharged to the vessel over a few weeks. Suitable elution kinetics of these agents, but also further agents to be used according to the present disclosure, are known in the prior art.

The stent degradation is to be viewed independently therefrom, because the stent main body has its function in the support of the vessel. A noteworthy collapsing pressure is to be withstood for at least two weeks, preferably 3 to 6 months. The complete stent degradation is accordingly to be completed up to 24 months, preferably 3 to 6 months, after loss of the collapsing pressure.

A further exemplary embodiment of a stent according to the present disclosure comprises a polymer layer which is applied to the surface or a part of the surface of the agent-containing layer c) and/or the partition layer b) and/or the main body a).

This exemplary embodiment is advantageous because, for one thing, the additional polymer layer provides the agents protection against abrasion, e.g., during storage or implantation. This polymer layer d) is preferably applied in a form-fitting manner to the abluminal surface of the stent according to the present disclosure.

Coating with the polymer layer d) only on the abluminal side of the stent surface is preferable because an additional luminal coating with polymer decelerates the degradation speed of the stent main body or possibly accelerates the degradation speed with magnesium alloys, because the pH value sinks upon hydrolytic cleavage of suitable polymers. Further advantages of the abluminal coating according to the step d) are avoiding undesired adhesion of the polymer to the carrier balloon (so-called "sticking") and a reduction of the profile of the stent (diameter of the stent crimped on the balloon).

Such a polymer layer d) (also called a topcoat) also offers an advantage if specific, preferably delayed elution kinetics of the agents is required. For example, if in spite of abluminal elution, an at least partial obstruction of the endothelialization by the antiproliferative action of the agent is to be prevented. The polymer layer d) is also preferably applied on the abluminal surface, more preferably on the surface or parts of the surface of the agent-containing layer c) and possibly the partition layer b).

If polymers are used for the agent-containing layer c) or the polymer-containing layer d), they are typically selected from the group consisting of:

nondegradable polymers: polyethylene; polyvinylchloride; polyacrylates; preferably polyethyl- and polymethylacrylates, polymethylmethacrylate, polymethyl-co-ethyl-acrylate, and ethylene/ethylacrylate; polytetrafluoroethylene, preferably ethylene/chlorotrifluoroethylene copolymers, ethylene/tetrafluoroethylene copolymers; polyamides, preferably polyamide-imide, PA-11, PA-12, PA-46, PA-66; polyetherimide; polyethersulfone; poly(iso)butylene; polyvinylchloride; polyvinylfluoride; polyvinylalcohol; polyurethane; polybutylene terephthalate; silicones; polyphosphazene; polymer foams, preferably polymer foams made of carbonates, styrenes; copolymers and/or blends of the listed polymer classes, polymers of the class of thermoplastics as well as degradable polymers: polydioxanone; polyglycolide; polycaprolactone; polylactides, preferably poly-L-lactide, poly-D,L-lactide, and copolymers and blends thereof, preferably poly(L-lactide-co-glycolide), poly(D,L-lactide-co-glycolide), poly(L-lactide-co-D,L-lactide), poly(L-lactide-co-trimethylene carbonate); triblock copolymers; polysaccharides, preferably chitosan, levan, hyaluronic acid, heparin, dextran, cellulose; polyhydroxyvalerate; ethylvinylacetate; polyethylene oxide; polyphosphorylcholine; fibrin; albumin; polyhydroxy butyric acid, preferably atactic, isotactic, and/or syndiotactic polyhydroxy butyric acid and their blends.

Especially preferred polymers for the agent-containing layer c) or polymer-containing layer d) of the present disclosure are the degradable polymers described hereinabove because no component foreign to the body remains in the organism due to the complete degradation of the polymers.

Furthermore, a stent according to the present disclosure is especially preferable if the partition layer b), over the entire period of time in which the agents are released from the stent main body and the stent main body is degraded, spatially separates the degradation products of the stent main body on one hand and the agents on the other hand as well as possibly the degradation products of the agent-containing layer c) and possibly the degradable, in particular, degradable under hydrolysis, polymer layer d).

Preferred partition layer materials for the partition layer b) comprise silicon carbide (SiC), Parylene (poly-paraxylylene), in particular, Parylene N, Parylene C, and Parylene D (GALXYL®), glycocalix, polysulfone, silicone rubber, polyurethane, hydroxylapitite, and/or diamond-like carbon.

The partition layer b) is preferably provided as a thin layer, preferably in the range of 100 nm to 5 µm, which is designed so that in the observed time window of a stent having noticeable collapsing pressure and/or a sustained agent elution, the thin layer represents a largely inert partition layer, which separates the agents on one hand and possibly the degradation products of the second layer c) and possibly the third polymer layer d) on the other hand. In addition, the partition layer b) preferably has good adhesion properties on the main body and to the layers c) and d), is flexible, and is distinguished by good biocompatibility.

Furthermore, a stent according to the present disclosure is preferred if the agents are suitable for prophylaxis and/or therapy of in-stent restenosis and/or tissue inflammation.

Preferred agents are particularly selected from the group consisting of lipid regulators, immunosuppressives, vasodilators, calcium channel blockers, calcineurin inhibitors, antiphlogistics, anti-inflammatory agents, antiallergy agents, oligonucleotides, estrogens, endothelium producers, steroids, proteins, peptides, proliferation inhibitors, analgesics, antirheumatics, and cytostatics, preferably cyclosporin A, paclitaxel, and limus compounds, preferably sirolimus (rapamycin), zotarolimus, tacrolimus, biolimus, everolimus.

The coating b) of the surface of the stent main body having the first preparation, preferably comprising SiC, parylene, hydroxylapatite, and/or diamond-like carbon according to the method for producing the stent is typically applied via plasma methods, the luminal surface of the stent main body is protected, for example, by heating a stent on a cylinder, a mandrel, a cannula, or the like, that the luminal surface of the stent main body is not coated by the first preparation. The coating having parylene is typically applied to the stent main body in vacuum by condensation from the gas phase as a preferably nonporous and transparent polymer film. Other preferred preparations, such as polysulfone, silicone rubber, is and/or polyurethane, may be applied by spraying and immersion methods, the luminal surface of the stent main body again being protected.

The coating of the surface of the partition layer from step b) on the abluminal side of the stent main body using the second agent-containing preparation c), so that an agent-containing layer c) is implemented according to the method of the present disclosure, may be performed by typical methods. In particular, a pure agent melt, an agent-solvent mixture, or an agent-polymer mixture may be used for the typical methods, such as immersion methods (dip coating), the stent main body being plugged onto a mandrel, spray coating using single or multiple material nozzles, rotary atomization and pressure nozzles, sputtering, or the like.

For precise dosing of the agents of the agent-containing layer c), the agent melt, the agent solution, or the agent incorporated in the polymer is painted on the stent main body, preferably using typical pipetting techniques. If the stent main body has notches in the form of dents or cups, the agent-containing preparation is preferably dosed into the notches, in particular, the dents or cups, using an agent jet.

Alternatively, the agent-containing layer may be poured in the form of regularly applied agent islands, preferably of equal size on a linear row on the partition layer b) (see, in particular, FIGS. 5 a) through 5 d)) on the stent struts and/or in suitable depressions, in particular, holes. The agent-containing layer c) may contain the agents, either homogeneously, in layers, or having a concentration gradient for one or more agents, possibly in an agent-carrier mixture.

A further conceivable coating method comprises a roller application, as shown in FIG. 1, in particular.

The coating of the surface of the stent produced according to a method of the present disclosure with the third preparation d), which comprises one or more polymers, so that a polymer layer d) is implemented, may also be performed using typical methods hereinabove described. If no polymer is to be provided on the luminal side, the luminal side of the surface of the stent main body is covered so that, during the coating method, this part of the surface does not come into contact with the polymer. A cylinder, a cannula, or a mantle is preferably used for this purpose. The cylinder, cannula or mantle is inserted longitudinally into the stent so that the luminal side of the surface of the stent main body covers it and is not coated by the polymer preparation.

If necessary, a typical drying step or other typical physical or chemical post-processing steps, such as vacuum or plasma treatment, may follow one or more coating steps before the stent is treated further.

BRIEF DESCRIPTION OF THE DRAWINGS

Various aspects of the present disclosure are described hereinbelow with reference to the accompanying figures in which like reference numbers refer to like parts throughout the views.

The figures show a coating method according to the present disclosure using a roller application on one hand and cross sections of the stent struts having coatings according to the present disclosure on the other hand. The present disclosure is not restricted to the web or strut geometries shown here, however, or to the exemplary embodiments of the coatings shown.

DETAILED DESCRIPTION

Figure 1:
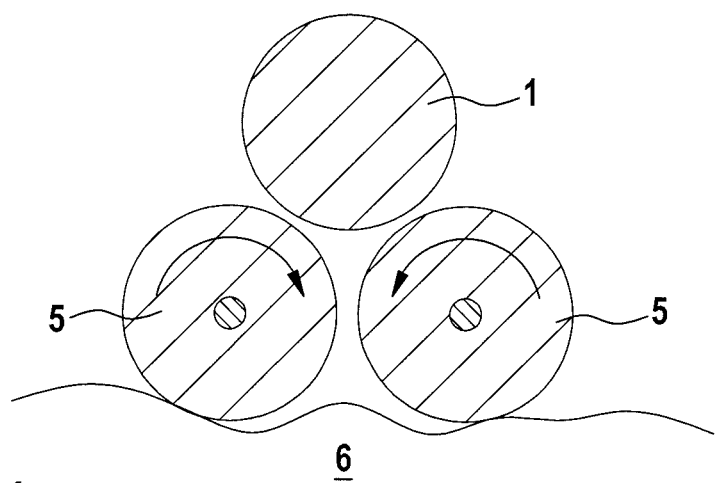
FIG. 1 is a schematic view of a stent having machines for roller application and coating medium.

FIG. 1 shows a stent main body 1 in cross-section and two rollers 5 in cross-section, the arrows indicating the movement directions of the particular rollers. In addition, the coating medium 6 is shown. The coating medium 6 may either represent the preparation of the agent-containing layer or alternatively the preparation of the polymer layer of the topcoat.

For a coating method according to a roller application, a stent main body 1 which already has a partition layer 2 (see FIG. 2) is brought into contact with the two rollers 5 rotating in opposite directions. As soon as the rollers 5 rotate in the direction of the movement arrows, the coating medium 6 is applied to the surface of the rollers 5 and thus to the abluminal surface of the stent main body 1. The stent main body 1 is preferably additionally rotated longitudinally to the axis so that the abluminal surface of the stent may be coated completely.

Figure 2:
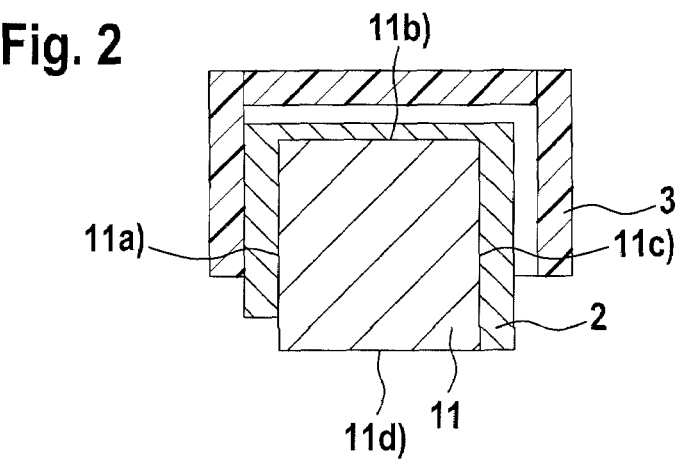
FIG. 2 is a cross-section view of a stent strut having partition layer b) and agent coating c)

FIG. 2 shows a stent strut 11 of a degradable metal stent 1, preferably a stent made of a magnesium alloy, in cross-section. The stent strut 11 itself is essentially rectangular, the edges being able to be rounded using electropolishing, which is performed after the laser cutting to shape. Furthermore, FIG. 2 shows a partition layer 2 which is in contact on three sides with the stent strut 11 a), 11 b), and 11 c). After implantation of the stent in a vessel, the sides 11 a), 11 b), and 11 c), preferably 11 b), of the stent strut 11 may be in contact with the vascular tissue and thus represent abluminal surfaces of the stent. In contrast thereto, the side 11 d) of the stent strut 11 faces toward the vascular lumen, i.e., is luminal, and is not covered by the inert partition layer 2. The stent struts 11 of a stent according to the present disclosure may thus degrade from the luminal side 11 d). The inert partition layer 2 is preferably connected in a formfitting manner to the surface 11 a), 11 b), and 11 c).

FIG. 2 shows the agent-containing layer 3, which covers the surface of the inner partition layer 2, which is applied to the sides 11 a), 11 b), and 11 c) of the stent strut, in a form-fitting manner. In the example shown in FIG. 2, the agent-containing layer 3 does not cover the entire partition layer 2, in particular, not in the end areas to the luminal side of the sides 11 a) and 11 c) of the stent strut 11.

The agent-containing layer 3 may comprise one or more agents and possibly comprise one or more polymers.

Figure 3:
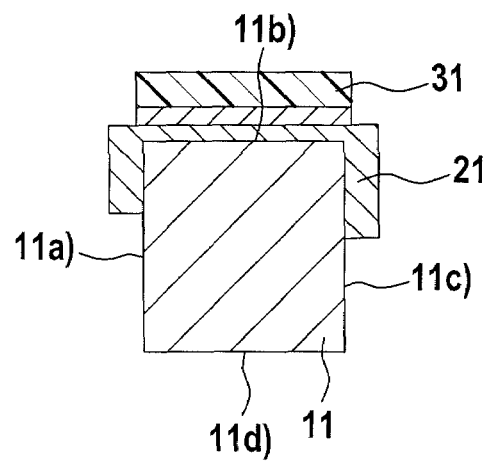
FIG. 3 is a cross-section view of a stent strut having partition layer b) and agent coating c)

FIG. 3 also shows a cross-section of a stent strut 11 of a stent 1 according to the present disclosure, the surface of the sides 11 a) and 11 b) of the stent strut being partially covered and the entire surface of the stent strut 11 b) being covered by the partition layer 21. The partition layer 21 is preferably connected in a form-fitting manner to the surface of the stent strut 11. In addition, FIG. 3 shows the agent-containing layer 31, which is applied to the surface of the partition layer 21 in the abluminal area of the side 11 b) of the stent strut. The agent-containing layer 31 is preferably connected in a form-fitting manner to the inner partition layer 21.

Figure 4:
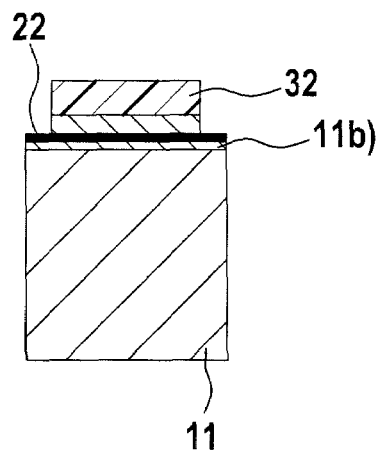
FIG. 4 is a cross-section view of a stent strut having partition layer b) and agent coating c)
Figure 5A:
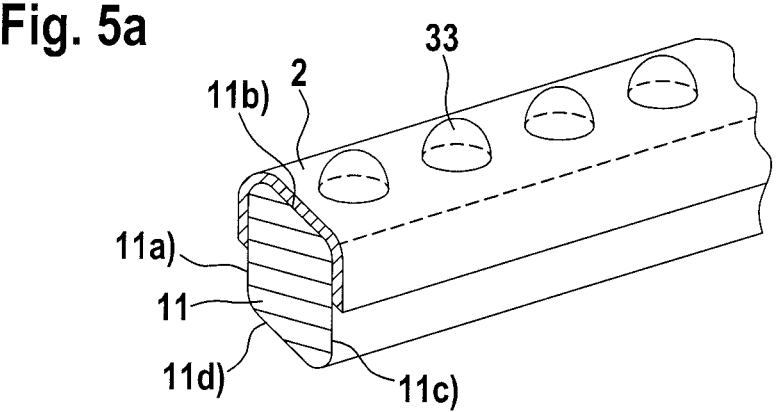
FIG. 5a is a perspective view of a stent strut having partition layer b) and agent coating c)
Figure 5B:
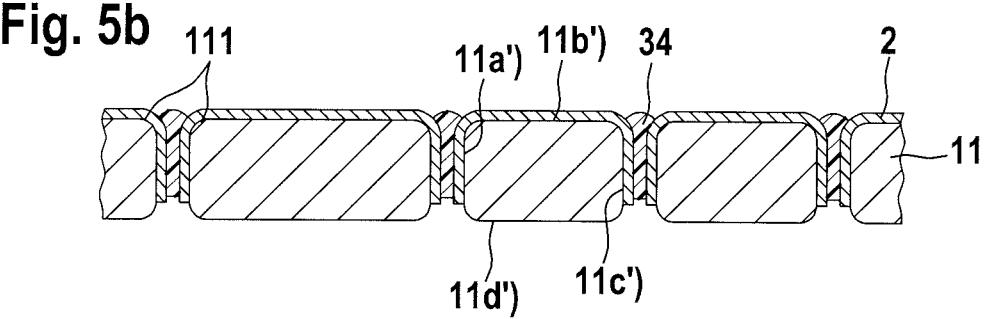
FIG. 5b is a cross-section view of a stent strut in the longitudinal direction having partition layers b) and agent coatings c)
Figure 5C:
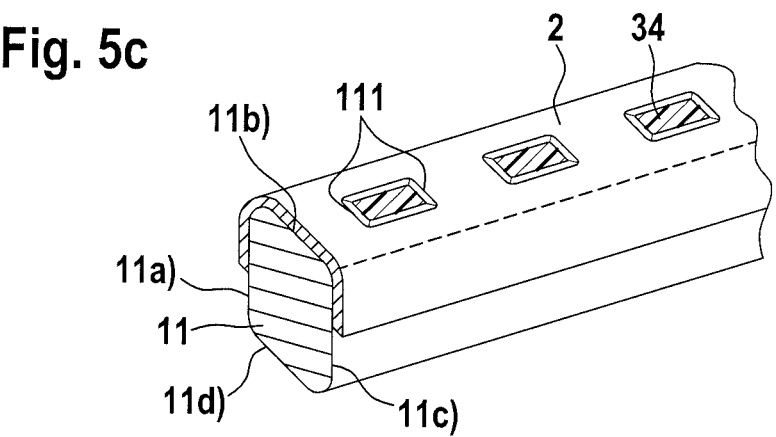
FIG. 5c is a perspective view of a stent strut having partition layer b) and agent coating c)
Figure 5D:
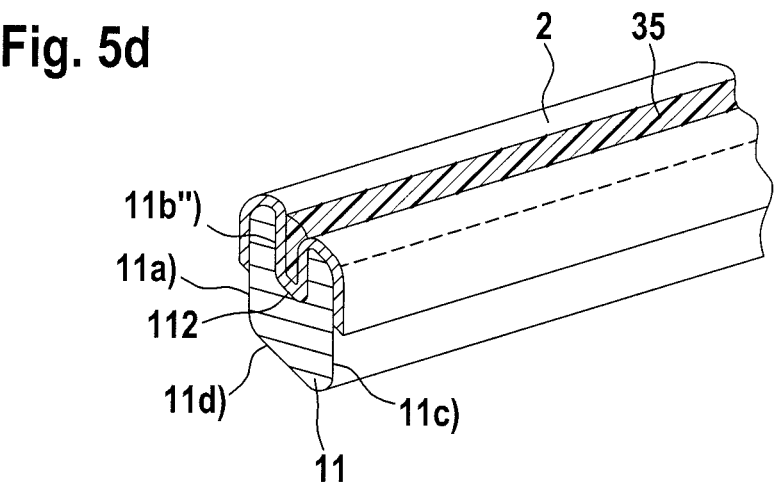
FIG. 5d is a perspective view of a stent strut having partition layer b) and agent coating c)

FIG. 4 also shows a cross-section of the stent strut 11 of a stent 1 according to the present disclosure, which has an inert partition layer 22 in the area of the surface 11 b) of the stent strut 11. In addition, FIG. 4 shows that the agent-containing layer 32 covers a part of the surface of the partition layer 22 on the abluminal side 11 b) of the stent strut 11. In the present exemplary embodiment, the agent-containing layer 32 also does not cover the entire area of the inert carrier layer 22.

FIG. 5 a shows a perspective view of a stent strut 11 as part of a complete stent design 1, the partition layer 2 being applied, in particular, to the sides 11 a), 11 b), and 11 c) of the stent strut 11. In addition, the stent strut 11 has agent islands 33, which are applied on the side 11 b) of the stent strut 11 on the surface of the partition layer 2. The agent islands 33 are provided in regularly-shaped agent islands which are situated in a straight line on the partition layer 2. Such a configuration allows the calculation of the agent release after implantation. The agent islands 33 may contain one or more agents, possibly distributed homogeneously in a carrier matrix or in layers, and, in particular, a concentration gradient may be implemented for one or more agents.

FIG. 5 b shows a cross-section of a stent strut 11 in the longitudinal direction to a complete stent design 1, in particular, of the CONOR® Stent, a design known in the art. Such a stent design according to CONOR® Stent is distinguished in that the stent struts have hollow passages 111, which penetrate a stent strut 11 from the abluminal side 11 b') to the luminal side 11 d'). The partition layer 2 is applied on the sides 11 a), 11 b), and 11 c) (not shown) and, in particular, on the sides 11 a'), 11 b'), and 11 c'). The agent coating 34 is provided in the hollow passages 111 of the stent struts 11, the hollow passages being able to be filled completely or partially with the agent coating 34. The agent coating 34 may contain one or more agents possibly in a carrier matrix in homogeneous distribution or in layers and, in particular, an agent gradient may be implemented for one or more agents.

FIG. 5 c shows a perspective view of a stent strut 11 of a stent design 1, as already described in FIG. 5 b, a partition layer 2 is at least partially applied to the sides 11 a), 11 b), and 11 c) of the stent strut 11. The agent coating 34 may be entirely or partially situated in the hollow cavities 111.

FIG. 5 d shows a perspective view of a stent strut 11 as part of a complete stent design 1. The stent strut 11 is distinguished in that the stent strut has a U-shaped notch or channel 112. The partition layer 2 is at least partially applied to the surface 11 a), 11 b), 11 b''), and 11 c). The agent layer 35 is situated in the U-shaped notch 112. The agent layer 35 may also only partially be provided in the U-shaped notch. The agent coating 35 may also contain one or more agents in homogeneous distribution, possibly in a carrier matrix, comprising multiple layers of one or more agents, and, in particular, one or more agent gradients of one or more agents may be incorporated herein.

Figure 6:
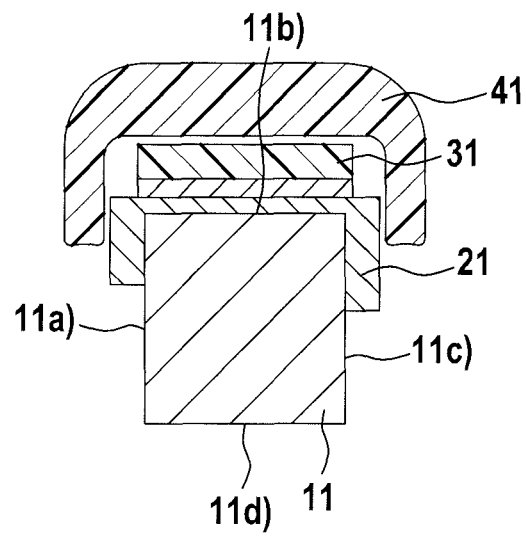
FIG. 6 is a cross-section view of a stent strut having partition layer b), agent coating c), and third polymer coating d) (topcoat)

FIG. 6 shows a stent strut of FIG. 3 and, in addition, a polymer layer 41 as a topcoat which covers the surface of the agent-containing layer 31 and partially covers the surface of the inert partition layer 21 on the sides 11 a) and 11 b) of the stent strut 11 of the stent 1 according to the present disclosure, preferably in a form-fitting manner.

The polymer layer 41 of the topcoat may comprise one or more polymers, preferably degradable polymers.

Figure 7:
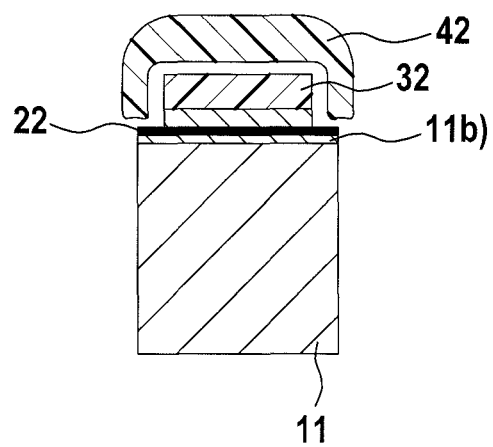
FIG. 7 is a cross-section view of a stent strut having partition layer b), agent coating c), and third polymer coating d) (topcoat)

FIG. 7 shows a stent strut 11 of a stent 1 according to the present disclosure having inert partition layer 22 and agent-containing layer 32 as shown in FIG. 4 and also a polymer layer 42 as a topcoat which covers the surface of the agent-containing layer 32 and partially covers the surface of the protruding inert partition layer 22, preferably in a form-fitting manner. The coating is only localized on the abluminal side 11 b) of the stent strut 11.

In FIGS. 2-7, stents coated according to the present disclosure are shown, wherein the stent main body may discharge agents to the vascular tissue, possibly with a delay, and simultaneously degrade upon and/or after implantation.

Figure 8:
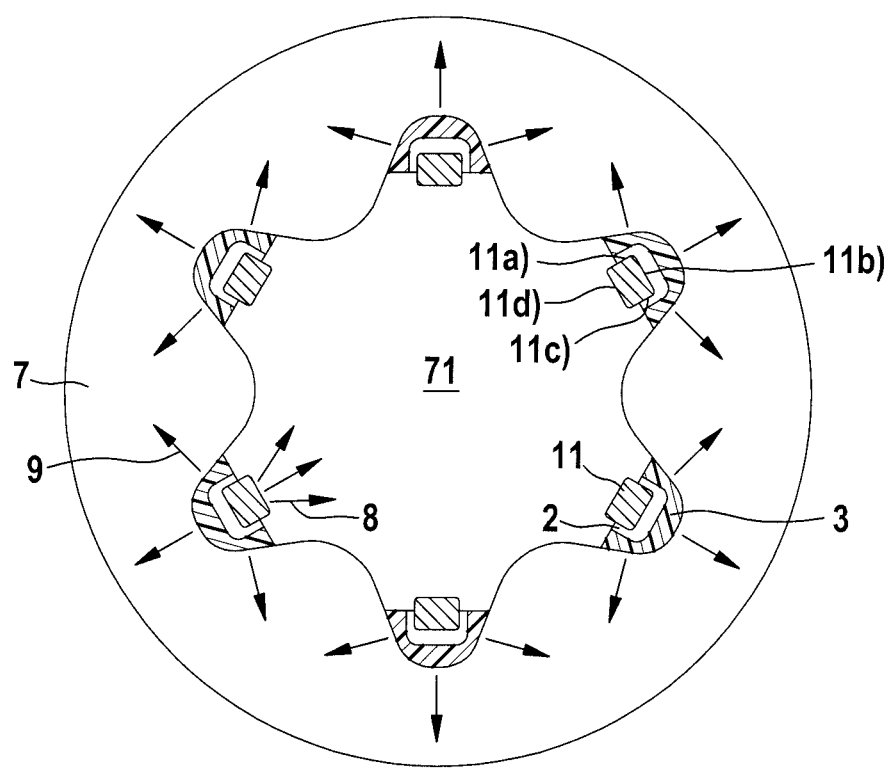
FIG. 8 is a cross-section view of a of a stent implanted in a vessel.

FIG. 8 shows a stent 1 according to the present disclosure which is implanted in vascular tissue 7, the stent 1 having six stent struts 11 having a luminal surface 11 d) and abluminal surfaces 11 a), 11 b), and 11 c). The number of the stent struts 11 is variable. In addition, the stent strut 11 is coated on the abluminal surfaces 11 a), 11 b), and 11 c) with an inert partition layer 2 and with an agent-containing layer 3. This coating preferably has a polymer layer as a topcoat 4 according to FIG. 6 or 7.

The diffusion direction of the degradation products of the stent main body according to the present disclosure into the vascular lumen 71 is shown by the arrows 8.

The diffusion direction of the agents of the agent-containing layer 3 into the vascular tissue 7 is shown in FIG. 8 by the arrows 9.

What is claimed is:

1. A stent, comprising:
    a) a degradable metal stent body having an external abluminal side, an internal luminal side and two connecting sides connecting the abluminal side to the luminal side;
    b) a partition layer which is applied to the surface of the stent main body so that at least part of the abluminal side and at least part of each but not the entirety of both of the two connecting sides are covered, and wherein at least part of the surface of the luminal side is not covered; and
    c) an agent-containing layer which is applied to the surface of the partition layer at least partially on the abluminal side and the two connecting sides of the stent main body, the agent-containing layer comprising one or more agents, the agent-containing layer being substantially not in direct contact with the stent main body,
    wherein the degradation products of the agent-containing layer and the degradation products of the stent main body are spatially separated by the partition layer so as to minimize any pH-lower effect of the degradation products of the stent main body on the degradation products of the agent-containing layer, and
    wherein the agent is suitable for at least one of prophylaxis, therapy of in-stent restenosis, and tissue inflammation.

2. The stent of claim 1, wherein said partition layer covers the entire length of one the two connecting sides.

3. The stent of claim 1, further comprising:
    d) a polymer layer which is applied to at least part of the surface of at least one of the agent-containing layer, the partition layer, and the stent main body.

4. The stent of claim 1, wherein the agent comprises at least one polymer selected from the group consisting of nondegradable polymers comprising polyethylene; polyvinylchloride; polyacrylates; polyethyl- and polymethylacrylates, polymethylmethacrylate, polymethyl-co-ethyl-acrylate, and ethylene/ethylacrylate; polytetrafluoroethylene, ethylene/chlorotrifluoroethylene copolymers, ethylene/tetrafluoroethylene copolymers; polyamides, polyamide imide, PA-11, PA-12, PA-46, PA-66; polyetherimide; polyethersulfone; poly(iso)butylenes; polyvinylchloride; polyvinylfluoride;

polyvinylalchohol; polyurethane; polybutylene terphthalate; silicones; polyphosphazene; polymer foams, polymer foams made of carbonates, styrenes; copolymers and blends of the listed polymer classes, polymers of the class of thermoplastics, degradable polymers comprising polydioxanone; polyglycolide; polycaprolactone; polylactides, poly-L-lactide, poly-D,L-lactide, and copolymers and blends thereof, poly(L-lactide-co-glycolide), poly(D,L-lactide-co-glycolide), poly(L-lactide-co-D,L-lactide), poly(L-lactide-co-trimethylene carbonate);triblock copolymers; polysaccharides, chitosan, levan, hylauronic acid, heparin, dextran, cellulose; polyhydroxyvalerate; ethylvinylacetate; polyethylene oxide; polyphosphorylcholine; fibrin; albumin; polyhydroxy butyric acid, atactic, isotactic, and syndiotactic polyhydroxy butyric acid and blends of the foregoing.

5. The stent of claim 4, wherein the at least one polymer is a degradable polymer.

6. The stent of claim 1, wherein either the degradable metal comprises either at least one degradable metal or degradable metal alloy selected from the group consisting of magnesium, iron, zinc, and tungsten.

7. The stent of claim 6, wherein the alloy is a magnesium alloy.

8. The stent of claim 7, wherein the magnesium alloy comprises yttrium.

9. The stent of claim 1, wherein over a period of time in which the agents are released from the stent and the stent main body is degraded, the partition layer spatially separates the degradation products of at least one of the stent main body, the agents and the degradation products of the agent-containing layer, and the polymer layer.

10. The stent of claim 1, wherein the partition layer comprises a material selected from the group consisting of silicon carbide (SiC), Parylene (poly-para-xylylene), glycocalix, polysulfone, silicone rubber, polyurethane, hydroxylapitite, and diamond-like carbon.

11. The stent of claim 1, wheren the partition layer has a thickness of 100 nm to 5 μm.

12. The stent of claim 1, wherein the agent is selected from the group consisting of lipid regulators, immunosuppressives, vasoldilators, calcium channel blockers, calcineurin inhibitors, antiphlogistics, anti-inflammatory agents, anti-allergy agents, oligonucleotides, estrogens, endothelium producers, steroids, proteins, peptides, proliferation inhibitors, analgesics, antirheumatics, and cytostatics.

13. A method for producing a stent, comprising:
a) providing a degradable metal stent main body having an external abluminal side, an internal luminal side and two connecting sides connecting the abluminal side to the luminal side, and a first preparation which comprises one or more substances;
b) coating the surface of the stent main body with the first preparation so that a partition layer is formed on at least part of the abluminal side and at least part of each but not the entirety of both of the two connecting sides, and wherein at least a part of the surface of the luminal side is not coated;
c) providing a second preparation which comprises one or more reagents; and
d) coating at least part of the surface of the partition layer on the abluminal side and the two connecting sides of the stent main body with the second preparation so that an agent-containing layer is formed;
wherein the agent is suitable for at least one of prophylaxis, therapy of in-stent restenosis, and tissue inflammation.

14. The method of claim 13, wherein in step b), the surface of the stent main body is coated on the abluminal side with the first preparation so that the partition layer is implemented on the abluminal side of the stent main body and the luminal side is not coated by the partition layer.

15. The method of claim 13, further comprising:
e) providing a third preparation comprising one or more polymers; and
f) coating the surface of the stent formed in step d) with the preparation so that a third polymer layer is formed the third layer covering at least a part of the surface of at least one of the agent-containing layer, the partition layer, and the stent main body without coating.

16. A method for the spatial separation of degradation products of a degradable metal stent main body and one or more agents and possibly one or more degradable polymer layers which are applied to a stent during or after implantation in a human or animal body, the method comprising:
a) providing a stent having
i) a degradable metal stent main body having an external abluminal side, an internal luminal side and two connecting sides connecting the abluminal side to the luminal side;
ii) a partition layer which is applied to the surface of the stent main body so that at least part of the abluminal side and at least part of each but not the entirety of both of the two connecting sides are covered, and at least a part of the surface of the luminal side is not covered; and
iii) an agent-containing layer which is applied to the surface of the partition layer at least partially on the abluminal side and the two connecting sides of the stent main body and not in direct contact with the stent main body, the agent containing layer comprising one or more agents suitable for at least one of prophylaxis, therapy of in-stent restenosis, and tissue inflammation; and,
b) implanting the stent in a human or animal body.

17. The method of claim 13, wherein the second preparation further comprises at least one polymer.

18. The stent of claim 1, wherein the agent containing layer covers the entirety of the abluminal side and less than the entirety of each connecting side.

* * * * *